United States Patent
Kim et al.

(10) Patent No.: US 9,289,178 B2
(45) Date of Patent: Mar. 22, 2016

(54) APPARATUS, UNIT MEASURER AND METHOD OF MEASURING BIOLOGICAL SIGNAL

(75) Inventors: Youn-ho Kim, Hwaseong-si (KR); Kun-soo Shin, Seongnam-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 439 days.

(21) Appl. No.: 13/185,766

(22) Filed: Jul. 19, 2011

(65) Prior Publication Data
US 2012/0232369 A1 Sep. 13, 2012

(30) Foreign Application Priority Data
Mar. 8, 2011 (KR) .................. 10-2011-0020615

(51) Int. Cl.
- *A61B 5/04* (2006.01)
- *A61B 5/00* (2006.01)
- *A61B 5/0428* (2006.01)
- *A61B 5/0402* (2006.01)

(52) U.S. Cl.
CPC .......... *A61B 5/7203* (2013.01); *A61B 5/0428* (2013.01); *A61B 5/04004* (2013.01); *A61B 5/04012* (2013.01); *A61B 5/04028* (2013.01); *A61B 5/7207* (2013.01); *A61B 5/7214* (2013.01); *A61B 5/7217* (2013.01); *A61B 5/7221* (2013.01)

(58) Field of Classification Search
CPC .......... A61B 5/04012; A61B 5/7203; A61B 5/7207; A61B 5/7214; A61B 5/7217; A61B 5/7221

USPC .................................... 600/547, 372
See application file for complete search history.

(56) References Cited

U.S. PATENT DOCUMENTS

| | | | | |
|---|---|---|---|---|
| 4,170,227 A * | 10/1979 | Feldman et al. | ............. | 600/517 |
| 5,682,902 A * | 11/1997 | Herleikson | ................... | 600/521 |
| 5,704,365 A * | 1/1998 | Albrecht et al. | ............. | 600/515 |
| 6,287,328 B1 * | 9/2001 | Snyder et al. | ................. | 600/509 |
| 7,092,750 B2 | 8/2006 | Van Ess | | |
| 2002/0077536 A1* | 6/2002 | Diab et al. | ..................... | 600/323 |
| 2004/0210148 A1* | 10/2004 | Van Ess | ........................ | 600/509 |
| 2008/0183090 A1* | 7/2008 | Farringdon et al. | ........... | 600/509 |

FOREIGN PATENT DOCUMENTS

| | | | | |
|---|---|---|---|---|
| JP | 06-030908 | 2/1994 | | |
| JP | 07-051239 | 2/1995 | | |
| JP | 2003-235823 | 8/2003 | | |
| JP | 2006231020 | * 7/2006 | .......... | A61B 5/0428 |
| JP | 2006-231020 | 9/2006 | | |
| KR | 10-2008-0097934 | 11/2008 | | |

* cited by examiner

*Primary Examiner* — Devin Henson
(74) *Attorney, Agent, or Firm* — NSIP Law

(57) ABSTRACT

A biological signal measuring apparatus is provided. The biological signal measuring apparatus includes a receiving unit configured to receive a biological signal from each of unit measurers arrayed on a subject's skin, and configured to receive a noise signal that is a common component of electrical characteristics, and a noise filtering unit configured to filter noise from a first biological signal between first electrodes of a first unit measurer among the unit measurers, by using a second noise signal between second electrodes of a second unit measurer among the unit measurers. The biological signal corresponds to a difference between the electrical characteristics of electrodes of each of the unit measurers.

21 Claims, 9 Drawing Sheets

APPARATUS, UNIT MEASURER AND METHOD OF MEASURING BIOLOGICAL SIGNAL

CROSS-REFERENCE TO RELATED APPLICATIONS

This application claims the benefit of Korean Patent Application No. 10-2011-0020615, filed on Mar. 8, 2011, in the Korean Intellectual Property Office, the entire disclosure of which is incorporated herein by reference for all purposes.

BACKGROUND

1. Field

The following description relates to an apparatus, a unit measurer, and a method of measuring a biological signal.

2. Description of the Related Art

Various medical devices for diagnosing a health condition of a patient are being used or developed. For patients' convenience in a health diagnosing process and for quickness of a health diagnosing result, medical devices for measuring patients' electrical biological signals including an electrocardiography (ECG) signal, a brain wave, an electromyogram signal or the like become more important. Since the biological signals are electrical signals, it is important to correctly measure the biological signals without noise.

SUMMARY

In one general aspect, a biological signal measuring apparatus is provided. The biological signal measuring apparatus includes a receiving unit configured to receive a biological signal from each of unit measurers arrayed on a subject's skin, and configured to receive a noise signal that is a common component of electrical characteristics, and a noise filtering unit configured to filter noise from a first biological signal between first electrodes of a first unit measurer among the unit measurers, by using a second noise signal between second electrodes of a second unit measurer among the unit measurers. The biological signal corresponds to a difference between the electrical characteristics of electrodes of each of the unit measurers.

The noise filtering unit may filter the noise from the first biological signal based on subtracting the second noise signal from the first biological signal.

The noise filtering unit may include a comparing unit configured to compare a first noise signal between first electrodes of a first unit measurer with the second noise signal, and an interference noise filtering unit configured to filter the noise from the first biological signal by using the second noise signal based on a result of the comparing.

In response to a difference between the first noise signal and the second noise signal being equal to or less than a threshold value based on the result of the comparing, the interference noise filtering unit may filter the noise from the first biological signal by using the second noise signal.

The second noise signal may be different from the first noise signal due to a difference between impedance between the first electrodes and impedance between the second electrodes.

The difference between the electrical characteristics may correspond to an electrical potential difference, and the common component of the electrical characteristics may correspond to a common voltage.

The difference between the electrical characteristics, and the common component may be detected by measurement electrodes among the first and second electrodes. The common component may be fed back to a ground voltage among the first and second electrodes.

The noise filtering unit may filter noise from a second biological signal between the second electrodes of the second unit measurer by using a first noise signal between the first electrodes of the first unit measurer.

A device may include the biological signal measuring apparatus.

In another aspect, a unit measurer is provided. The unit measurer includes a detecting unit configured to detect a biological signal from a difference between electrical characteristics of electrodes contacting a subject's skin, a noise detecting unit configured to detect a noise signal from a common component of the electrical characteristics of the electrodes, and configured to amplify the detected noise signal, and a communication unit configured to transmit the biological signal and the amplified noise signal to a biological signal measuring apparatus.

The amplified noise signal may be used in filtering noise of a biological signal of another unit measurer different from the unit measurer among a plurality of unit measurers arrayed on the subject's skin.

In yet another aspect, a biological signal measuring apparatus is provided. The biological signal measuring apparatus includes a detecting unit configured to detect a first biological signal from a difference between electrical characteristics of first electrodes contacting a subject's skin, a receiving unit configured to receive a second noise signal from a unit measurer arrayed on the subject' skin, and a noise filtering unit configured to filter noise from the first biological signal by using the second noise signal. The second noise signal is a common component of electrical characteristics of second electrodes of the unit measurer.

In yet another aspect, a method of measuring a biological signal is provided. The method includes receiving a biological signal from each of unit measurers arrayed on a subject' skin, receiving a noise signal from each of the unit measurers, and filtering noise from a first biological signal between first electrodes of a first unit measurer among the unit measurers, by using a second noise signal between second electrodes of a second unit measurer among the unit measurers. The biological signal is a difference between electrical characteristics of electrodes of each of the unit measurers.

The filtering of the noise may include subtracting the second noise signal from the first biological signal so as to filter the noise from the first biological signal.

The filtering of the noise may include comparing a first noise signal between first electrodes of a first unit measurer with the second noise signal, and filtering the noise from the first biological signal by using the second noise signal based on a result of the comparing.

In response to a difference between the first noise signal and the second noise signal being equal to or less than a threshold value based on the result of the comparing, the filtering of the noise may include the noise from the first biological signal by using the second noise signal.

The second noise signal may have a difference from the first noise signal based on a difference between impedance between the first electrodes and impedance between the second electrodes.

The difference between the electrical characteristics may correspond to an electrical potential difference, and the common component of the electrical characteristics may correspond to a common voltage.

The difference between the electrical characteristics, and the common component may be detected from measurement electrodes among the first and second electrodes, and the common component may be fed back to a ground voltage among the first and second electrodes.

The filtering of the noise may include filtering noise from a second biological signal between the second electrodes of the second unit measurer by using a first noise signal between the first electrodes of the first unit measurer.

A computer-readable recording medium may have recorded thereon a program for executing the method by using a computer.

In yet another aspect, an electronic device is provided. The electronic device includes a biological signal measuring unit including a first and second unit measurers disposed on a subject's skin, and spaced apart, a receiving unit configured to receive a biological signal corresponding with a difference between the electrical characteristics of electrodes of each of the first and second unit measurers, and configured to receive a noise signal that corresponds to a common component of electrical characteristics of each of the first and second unit measurers, and a noise filtering unit configured to filter noise from a first biological signal between first electrodes of the first unit measurer, by using a second noise signal between second electrodes of the second unit measurer, and a display unit configured to display a signal based on the first biological signal.

Other features and aspects may be apparent from the following detailed description, the drawings, and the claims.

Figure 1:
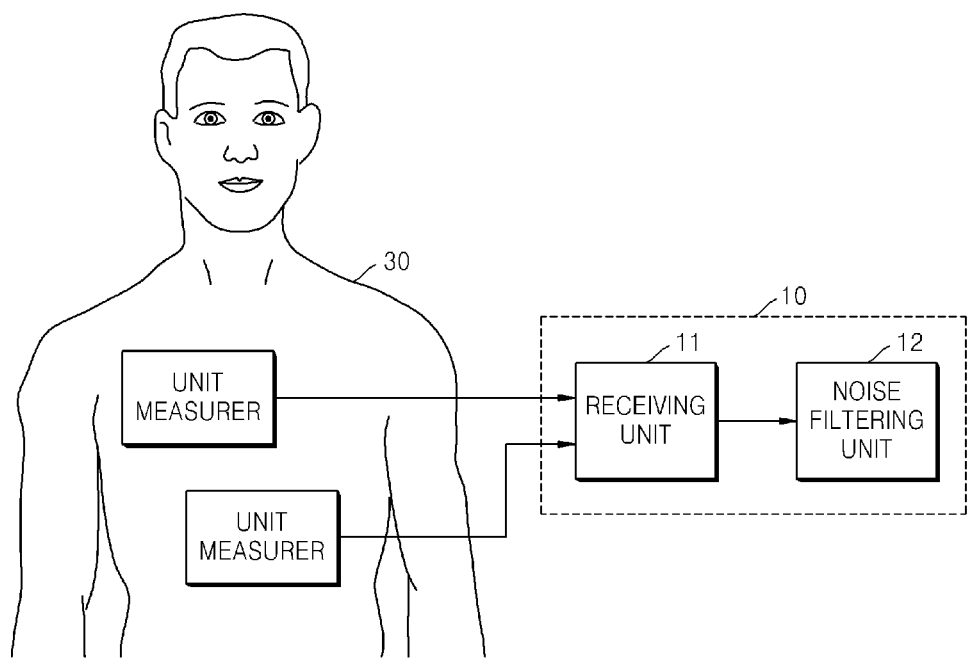
FIG. 1 illustrates an example of a biological signal measuring apparatus.

Throughout the drawings and the detailed description, unless otherwise described, the same drawing reference numerals will be understood to refer to the same elements, features, and structures. The relative size and depiction of these elements may be exaggerated for clarity, illustration, and convenience.

DETAILED DESCRIPTION

The following detailed description is provided to assist the reader in gaining a comprehensive understanding of the methods, apparatuses, and/or systems described herein. Accordingly, various changes, modifications, and equivalents of the systems, apparatuses and/or methods described herein will be suggested to those of ordinary skill in the art. Also, descriptions of well-known functions and constructions may be omitted for increased clarity and conciseness.

Reference will now be made to examples of which are illustrated in the accompanying drawings. In the following description, an example for measuring a biological signal of a subject is described. It is understood that one or more general configurations may be provided to the example for measuring the biological signal of the subject. For example, in order to recognize the biological signal, a configuration for displaying the biological signal of the subject on a screen or a paper may be provided to the example for measuring the biological signal of the subject.

FIG. 1 illustrates an example of a biological signal measuring apparatus 10. Referring to FIG. 1, the biological signal measuring apparatus 10 includes a receiving unit 11 and a noise filtering unit 12. However, the biological signal measuring apparatus 10 of FIG. 1 is an example, and thus it is understood that other implementations are within the scope of the teaching herein.

The receiving unit 11 receives a biological signal from each of unit measurers arrayed on a skin of a subject 30. The biological signal is detected based on a difference between electrical characteristics of electrodes of each of the unit measurers. For example, the difference between the electrical characteristics of the electrodes occurs based on electrical interfacing between the electrodes and the skin of the subject 30, and each of the unit measurers detects the difference between the electrical characteristics of the electrodes. The electrical characteristics may indicate electrical potential, and the difference between the electrical characteristics may indicate an electrical potential difference.

The biological signal may also include an electrocardiography (ECG) signal. The ECG signal indicates a graph-form signal that is a sum of action currents generated in systole and diastole of heart muscle of the subject 30, which are measured as an electrical potential difference at two external specific points on the subject 30. According to another aspect, the biological signal may include one or more other biological signals such as a brain wave signal, an electromyogram signal or the like, which may be electrically detected from a body of the subject 30.

The receiving unit 11 receives a noise signal from each of the unit measurers arrayed on the skin of the subject 30. The noise signal is detected from a common component of the electrical characteristics of the electrodes of each unit measurer. The electrical characteristic in each of the electrodes may be due to electrical interfacing between the electrodes and the skin of the subject 30, and the common component of the electrical characteristics may mean a signal component having a same or similar form included in each of the electrical characteristics of the electrodes. An example of the common component includes a common voltage waveform component to be described later.

Figure 2:
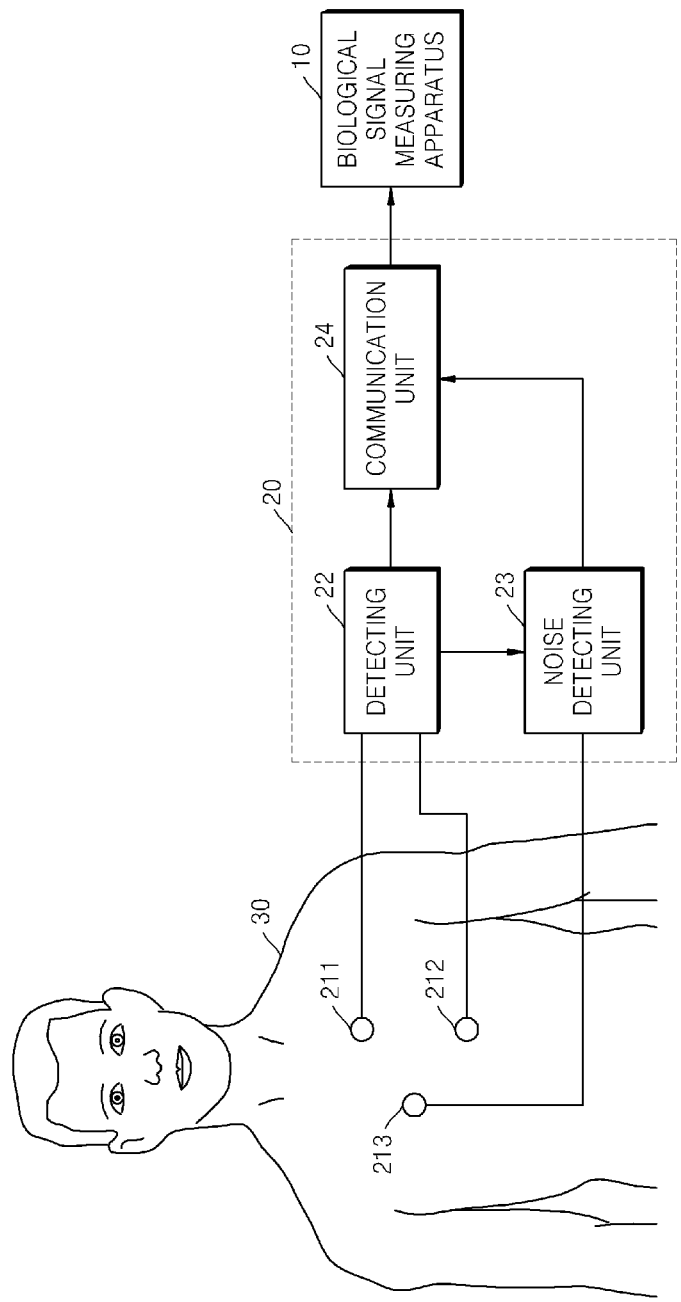
FIG. 2 illustrates an example of a unit measurer.

FIG. 2 illustrates an example of a unit measurere 20. Referring to FIG. 2, the unit measurere 20 includes a detecting unit 22, a noise detecting unit 23, and a communication unit 24. However, the unit measurere 20 is an example, and thus it is understood that other implementations are within the scope of the teaching herein.

The detecting unit 22 detects a biological signal based on a difference between electrical characteristics of electrodes contacting a subject's skin. Measurement electrodes 211 and 212 are positioned on the skin of a subject 30 and perform electrical interfacing with the skin of the subject 30. Based on the electrical interfacing, the detecting unit 22 detects a difference in electrical characteristics between the measurement electrodes 211 and 212. In the example, the difference in electrical characteristics may indicate an electrical potential difference. Also, based on the electrical potential difference, the detecting unit 22 generates a biological signal having a graph-form that repeatedly rises and falls over time.

Figure 3:
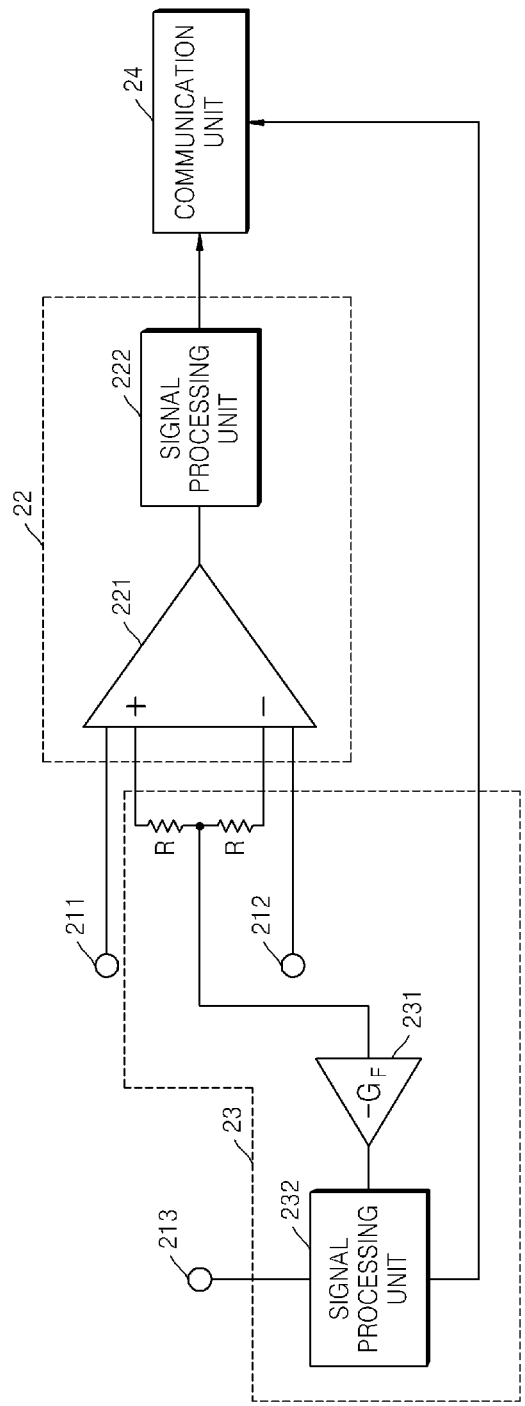
FIG. 3 illustrates an example of a detecting unit and an example of a noise detecting unit.

FIG. 3 illustrates an example of the detecting unit 22 and an example of the noise detecting unit 23. Referring to FIG. 3, the detecting unit 22 includes an amplifier 221 and a signal processing unit 222. Again, the detecting unit 22 of FIG. 3 is an example, and thus it is understood that other implementations are within the scope of the teaching herein.

The amplifier 221 amplifies a difference between electrical characteristics of measurement electrodes 211 and 212. For example, the amplifier 221 amplifies a difference between electrical potentials that are input from the measurement electrodes 211 and 212 to input terminals of the amplifier 221. An example of the amplifier 221 includes a differential amplifier or an instrumental amplifier, which is capable of measuring an electrical potential difference between the measurement electrodes 211 and 212. According to another aspect, the amplifier 221 may be replaced with a circuit, other than the differential amplifier or the instrumental amplifier, formed of passive and active devices to measure the electrical potential difference between the measurement electrodes 211 and 212.

Figure 4:
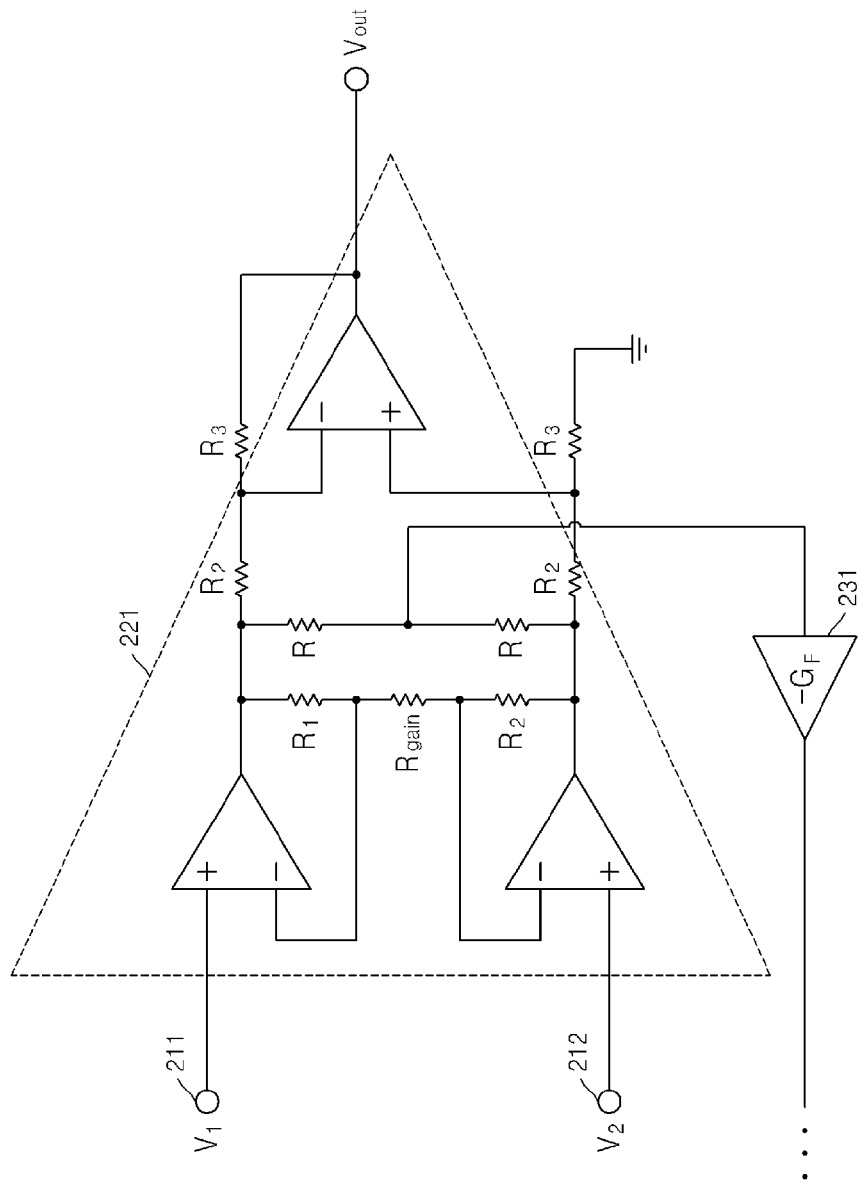
FIG. 4 illustrates an example of an amplifier and an example of another amplifier.

FIG. 4 illustrates an example of the amplifier 221 and an example of an amplifier 231. Referring to FIGS. 3 and 4, the amplifier 221 may be an instrumental amplifier detecting a difference between an electrical characteristic of the measurement electrode 211 and an electrical characteristic of the measurement electrode 212. In the example, the detected difference between the electrical characteristics is calculated by using Equation 1. In Equation 1, $V_{out}$ corresponds to the difference between the electrical characteristics. In other words, $V_{out}$ corresponds to an electrical potential difference; $V_1$ corresponds to the electrical characteristic of the measurement electrode 211. In other words, $V_1$ corresponds to electrical potential; $V_2$ corresponds to the electrical characteristic of the measurement electrode 212. In other words, $V_2$ corresponds to electrical potential; and $R_1$, $R_2$, $R_3$, and $R_{gain}$ corresponds to resistors forming the amplifier 221.

$$v_{out} = \left(1 + \frac{2R_1}{R_{gain}}\right)\frac{R_3}{R_2}(V_2 - V_1) \quad \text{[Equation 1]}$$

The signal processing unit 222 receives the detected difference between the electrical characteristics and then outputs a biological signal. As an example, the signal processing unit 222 may generate the biological signal based on the difference between the electrical characteristics which is detected based on at least one signal processing operation. Signal processing may involve extracting desired information from a signal, delivering or storing the information, or may involve performing processing on a signal so as to manage and control a system. Thus, the signal processing unit 222 may detect the difference between the electrical characteristics based on time as a signal having a graph-form, may filter noise from the detected signal, may amplify the signal, may convert the amplified analog signal into a digital signal, and may perform a calculation on the digital signal, so that the signal processing unit 222 may generate the biological signal. Based on the example, the signal processing unit 222 may include an amplifier for signal processing, an analog-to-digital (A/D) converter, a calculator, a noise filter, and the like.

The noise detecting unit 23 detects a noise signal from a common component of the electrical characteristics of the measurement electrodes 211 and 212, and amplifies the detected noise signal. The common component of the electrical characteristics of the measurement electrodes 211 and 212 may mean a signal component having substantially the same or a similar form included in each of the electrical characteristics of the measurement electrodes 211 and 212. For example, the common component indicates an electrical potential component included in all electrical potentials, such as, for example, the electrical characteristic of the measurement electrode 211 and the electrical characteristic of the measurement electrode 212. As another example, the common component may indicate a common voltage component included in both a voltage between the measurement electrode 211 and a ground electrode 213 and a voltage between the measurement electrode 212 and the ground electrode 213.

The common component of the electrical characteristics may be a result of a common-mode noise that is input to the subject 30 by a noise source around the subject 30. For example, a power line around the subject 30 causes the common-mode noise called 'an organic current' in the subject 30, and the electrical characteristic of the measurement electrode 211 and the electrical characteristic of the measurement electrode 212 commonly include a common component as a result of the organic current. However, since the common component may correspond with noise with respect to a biological signal, it may be filtered.

In order to filter the common component of the electrical characteristics of the measurement electrodes 211 and 212, the noise detecting unit 23 includes a Driven-Right Leg (DRL) circuit. The DRL circuit may function to feed back the common component of the electrical characteristics of the measurement electrodes 211 and 212 to the ground electrode 213. With reference to FIG. 3, the noise detecting unit 23 includes the DRL circuit and a signal processing unit 232. In the example, in order to detect the common component of the electrical characteristics of the measurement electrodes 211 and 212, the DRL circuit may be constituted by two equalization resistors R having the same value and an amplifier 231. The amplifier 231 may be an inverting amplifier that inverts and amplifies a common component detected from the two equalization resistors R. An output of the amplifier 231 is fed back to the ground electrode 213.

The signal processing unit 232 feeds back the output of the amplifier 231 to the ground electrode 213. Also, the signal processing unit 232 generates a noise signal based on the output of the amplifier 231. The signal processing unit 232 generates the noise signal based on the output of the amplifier 231, based on at least one signal processing operation. Signal processing may involve extracting desired information from a signal, delivering or storing the information, or may involve performing processing on a signal so as to manage and control a system. Thus, the signal processing unit 232 may detect a difference in the output of the amplifier 231 over time as a signal having a graph-form, may filter noise from the detected signal, may amplify the signal, may convert the amplified analog signal into a digital signal, and may perform a calculation on the digital signal, so that the signal processing unit 232 may generate a biological signal. Based on the example, the signal processing unit 232 may include, for example, an amplifier for signal processing, an A/D converter, a calculator, and a noise filter. Also, the signal processing unit 232 may amplify the noise signal, and use it in filtering noise of a biological signal of another unit measurer different from the unit measurere 20 from among a plurality of unit measurers arrayed on the skin of the subject 30.

The communication unit 24 transmits the biological signal and the amplified noise signal to the biological signal measuring apparatus 10. The communication unit 24 may transmit the biological signal and the amplified noise signal to the biological signal measuring apparatus 10 via one of various wired and/or wireless communication channels. Thus, the communication unit 24 may include a module for wired and/or wireless communication.

The electrodes 211, 212, and 213 of the unit measurere 20 may be positioned at regular short intervals. For example, the measurement electrodes 211 and 212 may be positioned at regular short intervals, and the measurement electrode 211 and the ground electrode 213 or the measurement electrode 212 and the ground electrode 213 may be positioned at regular short intervals. The electrodes 211, 212, and 213 that are positioned at regular short intervals allow the unit measurere 20 to be made smaller. For example, the electrodes 211, 212, and 213 positioned at regular short intervals are attached on one surface of the unit measurere 20, so that the unit measurere 20 may be implemented as a small ECG measuring apparatus that is portable and easy to use. As a non-limiting example, the regular short interval may be 2 cm.

The noise filtering unit 12 filters noise of a first biological signal between first electrodes of a first unit measurer among unit measurers by using noise of a second biological signal between second electrodes of a second unit measurer among the unit measurers. The noise filtering unit 12 may filter the noise of the first biological signal by subtracting the second biological signal from the first biological signal. This will now be described with reference to FIG. 5.

Figure 5:
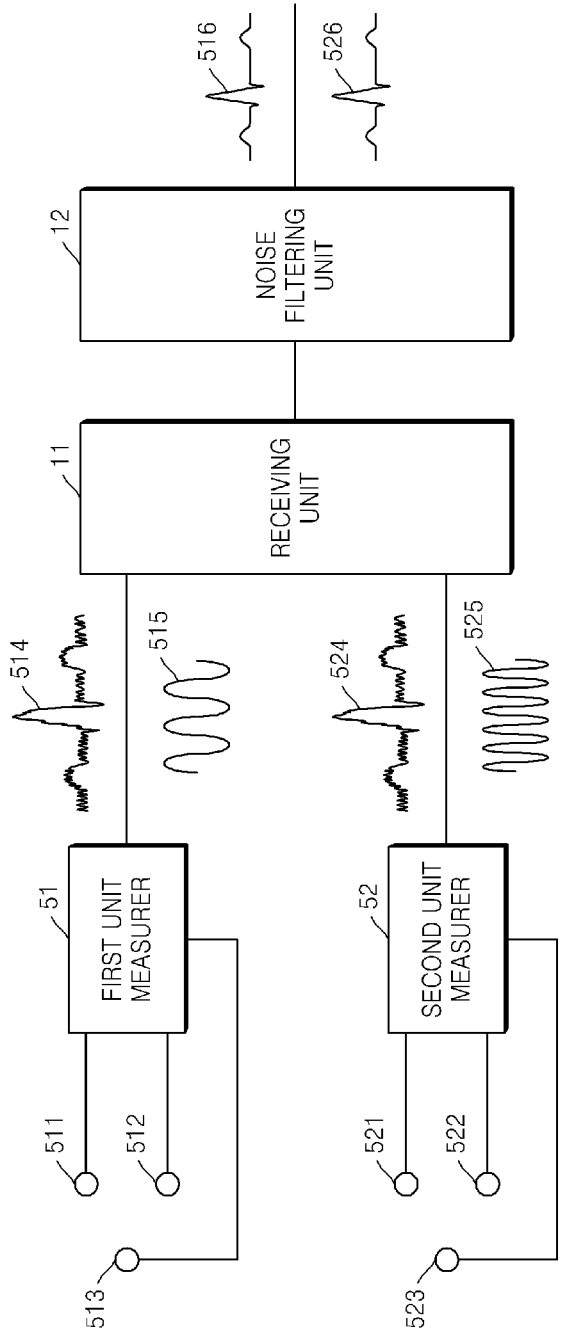
FIG. 5 illustrates an example of a receiving unit and an example of a noise filtering unit.

FIG. 5 illustrates the receiving unit 11 and the noise filtering unit 12. Referring to FIG. 5, the receiving unit 11 outputs a first biological signal 514 and a second noise signal 525, which are respectively received from a first unit measurer 51 and a second unit measurer 52 among unit measurers, to the noise filtering unit 12, and the noise filtering unit 12 generates a signal 516 by filtering the second noise signal 525 from the first biological signal 514. Also, the receiving unit 11 outputs a second biological signal 524 and a first noise signal 515, which are respectively received from the second unit measurer 52 and the first unit measurer 51, to the noise filtering unit 12, and the noise filtering unit 12 generates a signal 526 by filtering the first noise signal 515 from the second biological signal 524.

The first unit measurer 51 generates the first biological signal 514 by feeding back a common component of electrical characteristics of the first measurement electrodes 511 and 512 to a first ground electrode 513 by filtering noise due to the common component of the first measurement electrodes 511 and 512 via a DRL circuit. Also, the second unit measurer 52 generates the second biological signal 524 by feeding back a common component of electrical characteristics of the second measurement electrodes 521 and 522 to a second ground electrode 523 by filtering noise due to the common component of the second measurement electrodes 521 and 522 via a DRL circuit. Thus, the first biological signal 514 is a signal whereby noise due to the common component of the electrical characteristics of the first measurement electrodes 511 and 512 is filtered, and the second biological signal 524 is a signal whereby noise due to the common component of the electrical characteristics of the second measurement electrodes 521 and 522 is filtered.

However, the first biological signal 514 still may include the noise due to the common component of the second measurement electrodes 521 and 522, which is fed back to the second ground electrode 523. Similarly, the second biological signal 524 may still include the noise due to the common component of the first measurement electrodes 511 and 512, which is fed back to the first ground electrode 513. In other words, a biological signal detected by one of a plurality of unit measurers may include noise due to a common component fed back from another unit measurer among the plurality of unit measurers. Also, the noise due to the common component of the other unit measurer may be clearly detected in response to a difference existing between common components of the plurality of unit measurers. For example, if a difference exists between a common component fed back to the first ground electrode 513 and a common component fed back to the second ground electrode 523, the first biological signal 514 may include noise due to the common component fed back to the second ground electrode 523.

The difference between the common component of the first unit measurer 51 and the common component of the second unit measurer 52 may be incurred from a difference of measurement environment parameters between the first electrodes 511 and 512 and the second electrodes 521 and 522. For example, in a case where the first biological signal 514 and the second biological signal 524 are substantially simultaneously detected, a difference between measurement environment parameters of the first electrodes 511 and 512 and measurement environment parameters of the second electrodes 521 and 522, where the measurement environment parameters such as a breath of a subject, and an induced current or impedance by the power of the biological signal measuring apparatus 10, may cause the difference between the common component of the first unit measurer 51 and the common component of the second unit measurer 52. For similar reasons, the second noise signal 525 and the first noise signal 515 also have a difference therebetween.

The difference between the common component of the first unit measurer 51 and the common component of the second unit measurer 52 may increase in a case where the subject 30 is in an active condition such as, for example, walking or running, compared to a case where the subject 30 is in a stable condition, in response to a biological signal being detected. In addition, as described above, the common component is amplified by the inverting amplifier so that the common component may act as greater noise.

The noise filtering unit 12 subtracts the second noise signal 525 from the first biological signal 514, so that the noise filtering unit 12 filters the noise due to the common component of the second unit measurer 52 which is included in the first biological signal 514. Similarly, the noise filtering unit 12 subtracts the first noise signal 515 from the second biological signal 524, so that the noise filtering unit 12 filters the noise due to the common component of the first unit measurer 51 which is included in the second biological signal 524.

Figure 6:
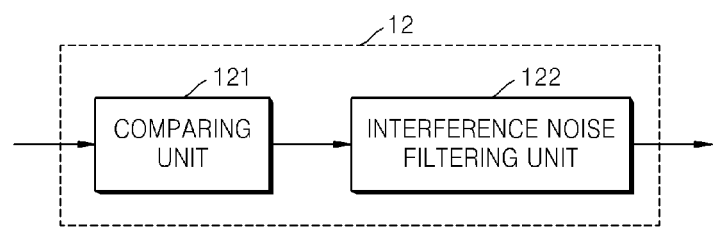
FIG. 6 illustrates an example of the noise filtering unit.

FIG. 6 illustrates an example of the noise filtering unit 12. As illustrated in FIG. 6, the noise filtering unit 12 includes a comparing unit 121 and an interference noise filtering unit 122. However, the noise filtering unit 12 of FIG. 6 is an example, and thus it is understood that other implementations are within the scope of the teaching herein.

The comparing unit 121 compares the second noise signal 525 with the first noise signal 515 between the first measurement electrodes 211 and 212 among first electrodes. The comparing unit 121 calculates a difference between a value of the first noise signal 515 and a value of the second noise signal 525, compares the calculated difference value with a threshold value, and determines whether the calculated difference value is equal to or greater than the threshold value. In the example, the first noise signal 515 and the second noise signal 525 have a graph-form that repeatedly rises and falls over time. Thus, the comparing unit 121 may synchronize the first noise signal 515 and the second noise signal 525 at a predetermined point of time, may calculate the difference between the value of the first noise signal 515 and the value of the second noise signal 525 based on time, may compare the calculated difference value with the threshold value, and may determine whether the calculated difference value is equal to or greater than the threshold value. The difference calculation may be performed by using various calculations performed in a time domain, a frequency domain, or any combination thereof. The threshold value may be determined by a user input. For example, if the threshold value is set while being close to 0, the threshold value may increase a filtering effect with respect to noise due to an interference signal.

Based on a result of the comparison, the interference noise filtering unit 122 filters the second noise signal 525 from the first biological signal 514. Based on the result of the comparison by the comparing unit 121, in response to the calculated difference value being equal to or greater than the threshold value, the interference noise filtering unit 122 subtracts the second noise signal 525 from the first biological signal 514. The first biological signal 514 and the second noise signal 525 have a graph-form that repeatedly rises and falls over time. Thus, the interference noise filtering unit 122 may synchronize the first biological signal 514 and the second noise signal 525 at a predetermined point of time, so that the interference noise filtering unit 122 may subtract the second noise signal 525 from the first biological signal 514. The subtraction may be performed by using various calculations performed in a time domain, a frequency domain, or any combination thereof.

Based on the example, the comparing unit 121 compares the first noise signal 515 with the second noise signal 525 between the second measurement electrodes 521 and 522 among the second electrodes of the second unit measurer 52, and based on a result of the comparison, the interference noise filtering unit 122 filters the first noise signal 515 from the second biological signal 524. The comparing unit 121 may calculate the difference between the value of the first noise signal 515 and the value of the second noise signal 525 based on time, may compare the calculated difference value with the threshold value, and may determine whether the calculated difference value is equal to or greater than the threshold value, and based on a result of the comparison by the comparing unit 121, in response to the calculated difference value being equal to or greater than the threshold value, the interference noise filtering unit 122 subtracts the first noise signal 515 from the second biological signal 524.

Figure 7:
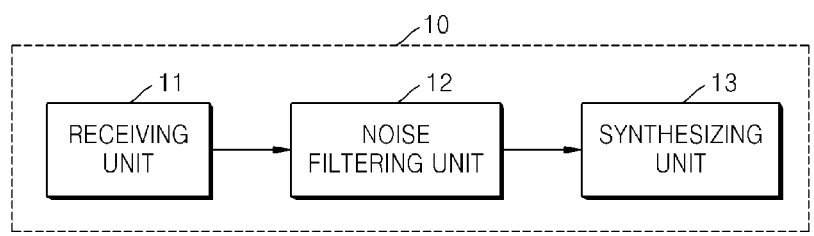
FIG. 7 illustrates another example of a biological signal measuring apparatus.

FIG. 7 illustrates another example of a biological signal measuring apparatus 10. As illustrated in FIG. 7, the biological signal measuring apparatus 10 also includes a synthesizing unit 13. The synthesizing unit 13 generates a biological signal by synthesizing a signal 516 obtained by filtering the second noise signal 525 from the first biological signal 514, and the signal 526 obtained by filtering the first noise signal 515 from the second biological signal 524. The signals 516 and 526 are detected in the form of a graph based on time. Thus, the synthesizing unit 13 may generate the biological signal based on the sum of the signals 516 and 526 by referring to at least one point among a plurality of points on a temporal axis of the graph of the signal 516. Also, the synthesizing unit 13 may generate the biological signal by synthesizing the first biological signal 514 and the second biological signal 524, and a noise filtering unit 12 may filter the first noise signal 515 or the second noise signal 525. The first electrodes 511, 512, and 513, and the second electrodes 521, 522, and 523 form pairs, respectively. The first electrodes 511, 512, and 513 may include the first measurement electrodes 511 and 512, and the first ground electrode 513, and the second electrodes 521, 522, and 523 may include the second measurement electrodes 521 and 522, and the second ground electrode 523. In another example, first electrodes and second electrodes may include measurement electrodes, and a first ground electrode and a second ground electrode may also be formed. The first electrodes 511, 512, and 513, and the second electrodes 521, 522, and 523 may each be formed as a wet-type electrode, a dry-type electrode, or the like. The wet-type electrode is formed so that a gel having an electrolyte component is coated on an electrode formed of a solid conductive material, and the gel contacts the skin of the subject 30. The dry-type electrode is formed so that an electrode formed of a solid conductive material directly contacts the skin of the subject 30.

The first measurement electrodes 511 and 512 are disposed at regular short intervals, and are adjacent to each other by a distance less than a distance between standard 12 lead electrodes. For example, the first measurement electrodes 511 and 512 may be disposed by having a distance of 2 cm therebetween. Also, each of the first measurement electrodes 511 and 512, and the first ground electrode 513 may be disposed by having a distance of 2 cm therebetween. Similarly, the second measurement electrodes 521 and 522 may be disposed at regular short intervals, and each of the second measurement electrodes 521 and 522, and the second ground electrode 523 may be disposed by having a regular short interval therebetween.

A plurality of unit measurers including the first unit measurer 51 and the second unit measurer 52 are arrayed on the skin of the subject 30 based on characteristics of contact parts of electrodes. The characteristics of the contact parts are determined based on a similarity in an electrical characteristic difference between the first measurement electrodes 511 and 512, and an electrical characteristic difference between the second measurement electrodes 521 and 522. An example of the electrical characteristic difference includes an electrical potential difference.

The unit measurers including the first unit measurer 51 and the second unit measurer 52 may be included in a pad. For example, the pad may be a patch-type pad that contacts the skin of the subject 30. The pad is formed of a first pad and a second pad, and the first unit measurer 51 is included in the first pad and the second unit measurer 52 is included in the second pad. In this case, the second pad may be positioned within a threshold distance from the first pad. The threshold distance may be, for example, 10 cm. Based on the example, the first unit measurer 51 and the second unit measurer 52 may be included in one pad. Also, the pad is formed of a nonconductor so as not to affect electrical interfacing between the electrodes and the skin of the subject 30. Examples of the nonconductor include various materials such as rubber, fiber, plastic, or the like. In another example, the first unit measurer 51 and the second unit measurer 52 may be formed as flexible circuit boards to be included in the pad. In yet another example, the first unit measurer 51 and the second unit measurer 52 may be detachable with respect to the pad.

The electrodes may be arrayed. The first electrodes 511, 512, and 513 may be arrayed in a pad including the first unit measurer 51, and the second electrodes 521, 522, and 523 may be arrayed in a pad including the second unit measurer 52. For example, the pad may be formed of a first pad and a second pad, and the first electrodes 511, 512, and 513 may be arrayed in the first pad, and the second electrodes 521, 522, and 523 may be arrayed in the second pad. Also, each of the first electrodes 511, 512, and 513 and the second electrodes 521, 522, and 523 may be arrayed in one pad. The electrodes may be detachable in relation to the pad. For example, the electrodes may be formed with a snap button to facilitate detachment from the pad.

The biological signal measuring apparatus 10 based on the example may include a display or may be connected to a display so as to show a biological signal being output from the signal 516, the signal 526, and the synthesizing unit 13. Also, the biological signal measuring apparatus 10 may be implemented as a portable terminal or an electronic device having one of various forms including a mobile phone, a personal digital assistant (PDA), a computer, or the like.

Figure 8:
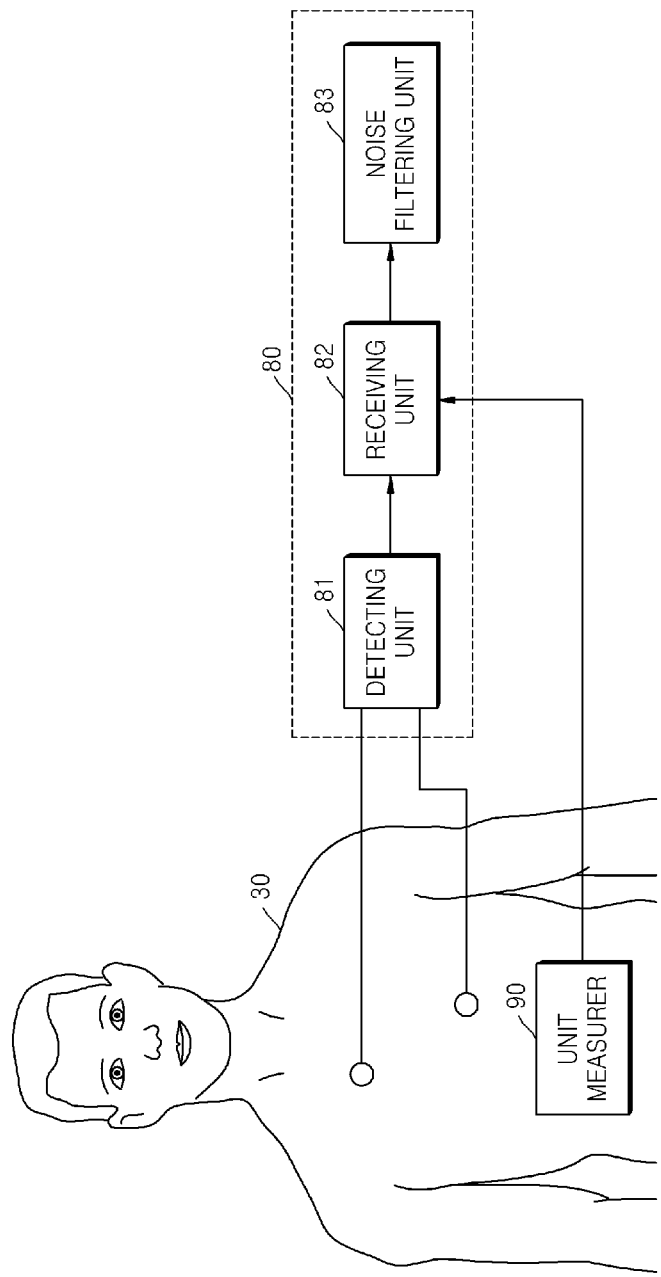
FIG. 8 illustrates yet another example of a biological signal measuring apparatus.

FIG. 8 illustrates yet another example of a biological signal measuring apparatus 80. Referring to FIG. 8, the biological signal measuring apparatus 80 includes a detecting unit 81, a receiving unit 82, and a noise filtering unit 83. However, the biological signal measuring apparatus 80 of FIG. 8 is an example, and thus it is understood that other implementations are within the scope of the teaching herein.

The detecting unit 81 detects a first biological signal based on a difference between electrical characteristics of first electrodes contacting the skin of a subject 30. Measurement electrodes among electrodes may perform electrical interfacing with the skin of the subject 30, and the detecting unit 81 may detect an electrical characteristic difference between the measurement electrodes, based on the electrical interfacing. Also, based on the electrical potential difference, the detecting unit 81 generates the first biological signal having a graph-form that repeatedly rises and falls over time.

The detecting unit 81 detects a first noise signal from a common component of the electrical characteristics of the first electrodes. The common component of the electrical characteristics of the first electrodes may mean a value that is commonly included in the electrical characteristics of the first electrodes. Since the common component acts as noise with respect to the first biological signal, the common component may be filtered. Thus, in order to efficiently filter the common component of the electrical characteristics of the first electrodes, the detecting unit 81 may include a DRL circuit. The DRL circuit is a circuit that feeds back the common component of the electrical characteristics of the first electrodes to a ground electrode.

Contents that are not described with respect to the detecting unit 81 may be substantially the same as the aforementioned contents described in relation to the detecting unit 22 and the noise detecting unit 23 in FIGS. 2 through 6, or is understood based on the aforementioned contents and that other implementations are within the scope of the teaching herein.

The receiving unit 82 receives a second noise signal from a unit measurer 90 arrayed on the skin of the subject 30, where the second noise signal is a common component of electrical characteristics of second electrodes of the unit measurer 90. Content that is not described with respect to the receiving unit 82 may be substantially the same as the aforementioned content described in relation to the receiving unit 11 that receives a second noise signal from a second unit measurer and that is described in FIGS. 1 through 6, or is understood based on the aforementioned content.

The noise filtering unit 83 filters the second noise signal from the first biological signal. Content that is not described in relation to the noise filtering unit 83 may be substantially the same as the aforementioned contents described in relation to the noise filtering unit 12 that filters a second noise signal from a first biological signal and that is described in FIGS. 1 through 6, or is understood based on the aforementioned contents.

Figure 9:
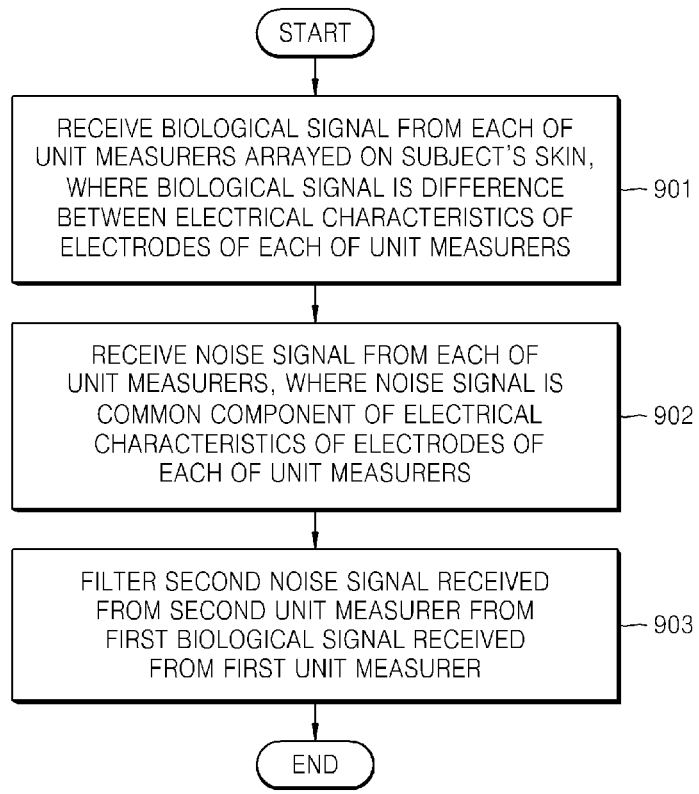
FIG. 9 is a flowchart illustrating an example of a method of measuring a biological signal.

FIG. 9 is a flowchart illustrating an example of a method of measuring a biological signal. The method includes operations processed in chronological order in the biological signal measuring apparatus 10 of FIG. 1. Thus, although some content is not described with respect to the method, in response to the content being substantially the same as the aforementioned contents described in relation to the biological signal measuring apparatus 10 or is understood based on the aforementioned content, the content may also be applied to the example of the method of FIG. 9.

In operation 901, the receiving unit 11 receives a biological signal from each of unit measurers arrayed on a subject's skin, where the biological signal is a difference between electrical characteristics of electrodes of each of the unit measurers. In operation 902, the receiving unit 11 receives a noise signal from each of the unit measurers, where the noise signal is a common component of the electrical characteristics of the electrodes of each of the unit measurers. In operation 903, the noise filtering unit 12 filters noise from a first biological signal received from a first unit measurer, based on a second noise signal received from a second unit measurer.

Figure 10:
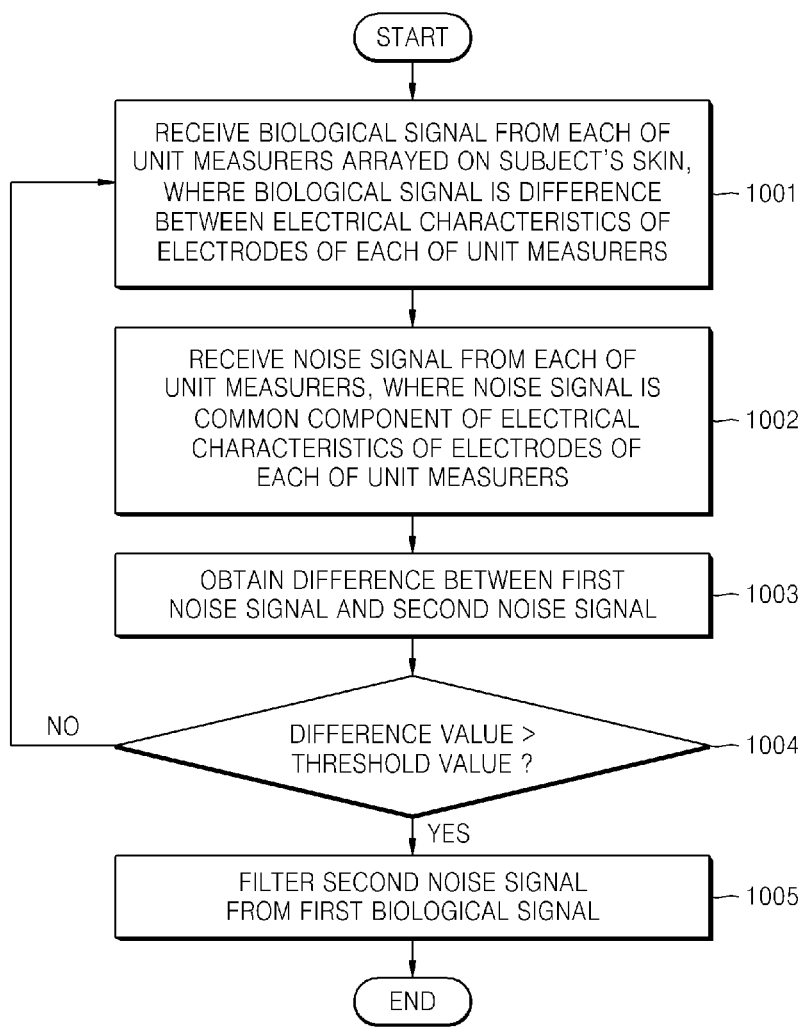
FIG. 10 is a flowchart illustrating another example of a method of measuring a biological signal.

FIG. 10 is a flowchart illustrating an example of a method of measuring a biological signal. The method includes operations processed in chronological order in the biological signal measuring apparatus 10 of FIG. 1. Thus, although some content is not described in relation to the method, in response to the content being substantially the same as the aforementioned content about the biological signal measuring apparatus 10 or is understood based on the aforementioned content, the content may also be applied to the method of FIG. 10.

In operation 1001, the receiving unit 11 receives a biological signal from each of unit measurers arrayed on a subject's skin, where the biological signal is a difference between electrical characteristics of electrodes of each of the unit measurers. In operation 1002, the receiving unit 11 receives a noise signal from each of the unit measurers, where the noise signal is a common component of the electrical characteristics of the electrodes of each of the unit measurers. In operation 1003, the comparing unit 121 compares a first noise signal between first electrodes of a first unit measurer with a second noise signal between second electrodes of a second unit measurer. In operation 1004, the comparing unit 121 determines whether a difference between the first noise signal and the second noise signal is equal to or less than a threshold value. In operation 1005, in response to the difference between the first noise signal and the second noise signal being equal to or less than the threshold value based on a result of the comparison, the interference noise filtering unit 122 filters noise from a first biological signal based on the second noise signal.

As described above, based on the one or more of the above examples, biological signals measured by using multiple unit measurers are compared or synthesized to provide ease of portability, convenience of use, and measurement efficiency, and noise due to interference between the multiple unit measurers is filtered so that the biological signals of a subject may be more accurately measured.

Program instructions to perform a method described herein, or one or more operations thereof, may be recorded, stored, or fixed in one or more computer-readable storage media. The program instructions may be implemented by a computer. For example, the computer may cause a processor to execute the program instructions. The media may include, alone or in combination with the program instructions, data files, data structures, and the like. Examples of computer-readable media include magnetic media, such as hard disks, floppy disks, and magnetic tape; optical media such as CD ROM disks and DVDs; magneto-optical media, such as optical disks; and hardware devices that are specially configured to store and perform program instructions, such as read-only memory (ROM), random access memory (RAM), flash memory, and the like. Examples of program instructions include machine code, such as produced by a compiler, and files containing higher level code that may be executed by the computer using an interpreter. The program instructions, that is, software, may be distributed over network coupled computer systems so that the software is stored and executed in a distributed fashion. For example, the software and data may be stored by one or more computer readable recording mediums. Also, functional programs, codes, and code segments for accomplishing the example embodiments disclosed herein can be easily construed by programmers skilled in the art to which the embodiments pertain based on and using the flow diagrams and block diagrams of the figures and their corresponding descriptions as provided herein. Also, the described unit to perform an operation or a method may be hardware, software, or some combination of hardware and software. For example, the unit may be a software package running on a computer or the computer on which that software is running.

A number of examples have been described above. Nevertheless, it will be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. A biological signal measuring apparatus comprising:
a receiving unit configured to receive a first biological signal and a first noise signal from a first unit measurer arrayed on a subject's skin through a noise detecting unit and to receive a second biological signal and a second noise signal from a second unit measurer arrayed on the subject's skin through the noise detecting unit, the first biological signal corresponding to a difference between electrical characteristics of first electrodes of the first unit measurer, the first noise signal being generated based on a common component detected from electrical characteristics of the first electrodes of the first unit measurer, the second biological signal corresponding to a difference between electrical characteristics of second electrodes of the second unit measurer, and the second noise signal being generated based on a common component detected from electrical characteristics of the second electrodes of the second unit measurer, wherein the noise detecting unit is configured to amplify and invert the first noise signal and amplify the second noise signal; and
a noise filtering unit configured to filter noise from the first biological signal between the first electrodes of the first unit measurer among the two unit measurers, using the second noise signal between second electrodes of the second unit measurer among the two unit measurers.

2. The biological signal measuring apparatus of claim 1, wherein the noise filtering unit filters the noise from the first biological signal by subtracting the second noise signal from the first biological signal.

3. The biological signal measuring apparatus of claim 1, wherein the noise filtering unit comprises:
a comparing unit configured to compare the first noise signal between the first electrodes of the first unit measurer with the second noise signal between the second electrodes of the second unit measurer; and
an interference noise filtering unit configured to filter the noise from the first biological signal using the second noise signal based on a result of the comparing.

4. The biological signal measuring apparatus of claim 3, wherein, in response to a difference between the first noise signal and the second noise signal being equal to or less than a threshold value based on the result of the comparing, the interference noise filtering unit filters the noise from the first biological signal by using the second noise signal.

5. The biological signal measuring apparatus of claim 3, wherein the second noise signal is different from the first noise signal due to a difference of impedance between the first electrodes and impedance between the second electrodes.

6. The biological signal measuring apparatus of claim 1, wherein the difference between the electrical characteristics corresponds to an electrical potential difference, and the common component of the electrical characteristics corresponds to a common voltage.

7. The biological signal measuring apparatus of claim 1, wherein the difference between the electrical characteristics and the common component are each detected by measurement electrodes from among the first and second electrodes, and the common component is fed back to a ground voltage among the first and second electrodes.

8. The biological signal measuring apparatus of claim 1, wherein the noise filtering unit filters noise from the second biological signal between the second electrodes of the second unit measurer using the first noise signal between the first electrodes of the first unit measurer.

9. The biological signal measuring apparatus of claim 1, further comprising a display unit configured to display a signal based on the first biological signal.

10. The biological signal measuring apparatus of claim 1, wherein the common component is a voltage waveform component generated by the first electrodes of the first unit measurer and by the second electrodes of the second unit measurer that is the same or approximately the same in form over a period of time.

11. The biological signal measuring apparatus of claim 1, wherein the common component is a voltage waveform component between a first measurement electrode and a third measurement electrode and a voltage waveform component between a second measurement electrode and the third measurement electrode that is the same or approximately the same in form over a period of time.

12. A biological signal measuring apparatus comprising:
a detecting unit configured to detect a first biological signal from a difference between electrical characteristics of first electrodes of a first unit measurer contacting a subject's skin;
a noise detecting unit configured to detect a first noise signal and a second noise signal from a common component of the electrical characteristics of the electrodes, and configured to amplify and invert the first noise signal and amplify the second noise signal;
a receiving unit configured to receive the second noise signal from a second unit measurer arrayed on the subject' skin, the second noise signal being generated based on a common component detected from electrical characteristics of second electrodes of the second unit measurer; and
a noise filtering unit configured to filter noise from the first biological signal using the second noise signal.

13. A method of measuring a biological signal, the method comprising:
receiving a first biological signal from a first unit measurer arrayed on a subject's skin and a second biological signal from a second unit measurer arrayed on the subject's skin, the first biological signal corresponding to a difference between electrical characteristics of first electrodes of the first unit measurer and the second biological signal corresponding to a difference between electrical characteristics of second electrodes of the second unit measurer;

receiving a first noise signal from the first unit measurer and a second noise signal from the second unit measurer, the first noise signal being generated based on a common component detected from electrical characteristics of the first electrodes of the first unit measurer and the second noise signal being generated based on a common component detected from electrical characteristics of second electrodes of the second unit measurer;

amplifying and inverting the first noise signal;

amplifying the second noise signal; and filtering noise from the first biological signal between the first electrodes of the first unit measurer among the two unit measurers, using the second noise signal between the second electrodes of the second unit measurer among the two unit measurers.

14. The method of claim 13, wherein the filtering of the noise comprises subtracting the second noise signal from the first biological signal so as to filter the noise from the first biological signal.

15. The method of claim 13, wherein the filtering of the noise comprises comparing the first noise signal between the first electrodes of the first unit measurer with the second noise signal, and filtering the noise from the first biological signal by using the second noise signal based on a result of the comparing.

16. The method of claim 15, wherein, in response to a difference between the first noise signal and the second noise signal being equal to or less than a threshold value based on the result of the comparing, the filtering of the noise comprises filtering the noise from the first biological signal by using the second noise signal.

17. The method of claim 15, wherein the second noise signal has a difference from the first noise signal based on a difference of impedance between the first electrodes and impedance between the second electrodes.

18. The method of claim 13, wherein the difference between the electrical characteristics corresponds to an electrical potential difference, and the common component of the electrical characteristics corresponds to a common voltage.

19. The method of claim 13, wherein the difference between the electrical characteristics and the common component are each detected by measurement electrodes from among the first and second electrodes, and the common component is fed back to a ground voltage among the first and second electrodes.

20. The method of claim 13, wherein the filtering of the noise comprises filtering noise from the second biological signal between the second electrodes of the second unit measurer using the first noise signal between the first electrodes of the first unit measurer.

21. A non-transitory computer-readable recording medium having recorded thereon a program for executing the method of claim 13, by using a computer.

* * * * *